United States Patent [19]
Barsom

[11] Patent Number: 4,742,833
[45] Date of Patent: May 10, 1988

[54] DEVICE FOR TREATING MALE PERSONS SUFFERING FROM URINE INCONTINENCE

[75] Inventor: Shafik Barsom, Hanover, Fed. Rep. of Germany

[73] Assignee: Richard Wolf GmbH, Fed. Rep. of Germany

[21] Appl. No.: 796,246

[22] Filed: Nov. 8, 1985

[30] Foreign Application Priority Data

Jan. 3, 1985 [DE] Fed. Rep. of Germany ....... 3500047

[51] Int. Cl.⁴ ............................................. A61N 1/04
[52] U.S. Cl. ..................................... 178/794; 128/421
[58] Field of Search ............ 128/128 NR, 419 R, 421, 128/783, 788, 794, 802, DIG. 25

[56] References Cited

U.S. PATENT DOCUMENTS

| 396,212 | 1/1889 | Long | 128/794 |
| 427,468 | 5/1890 | Dow | 128/794 |
| 522,841 | 7/1894 | Lawlor | 128/794 |
| 1,266,393 | 5/1918 | Bowen | 128/794 |
| 3,403,684 | 10/1968 | Stiebel et al. | 128/788 |
| 3,870,051 | 3/1975 | Brindley | 128/419 E |
| 4,387,719 | 6/1983 | Plevnik et al. | 128/419 E |
| 4,406,288 | 9/1983 | Horwinski | 128/788 |

Primary Examiner—William E. Kamm
Attorney, Agent, or Firm—Hill, Van Santen, Steadman & Simpson

[57] ABSTRACT

A device for treating male persons suffering from urine incontinence consists of a carrier having an aperture for surrounding the penis of the patient, the carrier having at least two electrodes, which are mounted in the aperture for engaging the opposite sides of the penis and are connected to one pole of a current source, and the carrier on a surface which faces towards the body of the person wearing the device having a plurality of electrodes which are connected to another pole of the current source so that the device can electro-stimulate closure muscles for the bladder.

9 Claims, 3 Drawing Sheets

DEVICE FOR TREATING MALE PERSONS SUFFERING FROM URINE INCONTINENCE

Urine incontinence is a problem widespread in men of increasing age. There may be various causes. They may be based on functional disorders, e.g. a neurosis or psychosis, or they may have an anatomical foundation, e.g. insufficiency or failure of the sphincter due to weakness of the support and suspension system, but may also be the result of an adenoma of the prostate, i.e. a morbid enlargement of the prostate gland, so that the urethra becomes squashed, so impeding emptying of the bladder to the extent that urination becomes impossible and it is only the pressure built up from the kidneys which forces the urine through the constricted urethra in dropwise fashion.

Uncontrolled emission of urine is a sympton which is subjectively extremely unpleasant for the person concerned since in the past no aids have been available which offer a satisfactory solution to the problem.

It is known to use napkin-like liners in underclothes to soak up dribbled urine. Such liners cannot however be made gas proof and so very frequent changing is required in order to prevent decomposition of the urine, giving rise to the formation of an odour which is perceived by the people around, so publishing the ailment.

Another means involves a condom-like receiving container, which does however have the disadvantage of adversely affecting the circulation if worn continuously.

Furthermore, it is known to use a bag consisting on the inside of highly absorbent material which is adapted to be pushed onto the penis and fixed to the underclothes by an adhesive strip.

All these known solutions have the disadvantage that the penis remains in contact with the emerging urine so that irritation can result from permanent contact with moisture.

The decisive disadvantage of the known devices, however, resides in the fact that they are all based on remedying the consequences of urination which has already commenced, whereas it would actually be desirable to take measures to remedy the undesired emergence of urine.

In order to treat urine incontinence in female persons, it is known to prevent an undesired flow of urine by using current pulses to stimulate the bladder-closing muscle tissue. Such a measure is facilitated by the anatomy of the female sexual organs, since it is possible to locate the electrodes in the immediate vicinity of the closure muscle tissue whether by using an intravaginal carrier or a carrier of which the electrodes can be disposed to bear on the patient's vulva immediately in the region of the urethra exit (German Patent Application No. P 33 17 118.1 and its corresponding U.S. Pat. No. 4,580,578).

In a man, the urethra and the closure muscle system are not immediately accessible so that in the past it was not thought possible to provide a solution involving electrical stimulation similar to the known apparatus for women.

SUMMARY OF THE INVENTION

The invention is based on the problem of providing a device for treating male persons suffering from urine incontinence and which is likewise based on using current pulses for stimulation.

According to the invention, the problem posed is resolved in that the device consists of a carrier having an aperture and enclosing the penis at its root and comprising at least two electrodes which are connected to one pole of a current source and which rests on the penis, and in that on the side of the carrier which is towards the body of the person there are a plurality of electrodes connected to the other pole of the current source, which in a per se known manner is provided by a pulse generator operated by a voltage source.

The success of the invention lies in the particular arrangement of electrodes. In the region of the penis root, the penis is enclosed by electrodes disposed concentrically of the urethra and which are of one polarity, while the counter electrodes act on the abdomen so that a flow of current through the closure muscle tissue is produced. It has been found that when the closure muscle tissue can be so stimulated by this arrangement of electrodes, an uncontrolled emergence of urine can be avoided. In consequence, problems of hygiene due to emerging urine are completely eliminated and there can be no irritation of the skin due to contact with urine which has so emerged.

In a further development of the invention, the electrodes which are applied to the penis consist of two elements which are elastically deformable or which can be deflected outwardly against spring force and relative to each other.

There are countless ways of constructing the electrodes. A preferred embodiment resides in the electrodes consisting of two elements disposed opposite each other in the aperture and symmetrically of its central axis and having convexly curved surfaces, at least one of which is mounted in the carrier for radially outwards movement against a spring force.

Another advantageous embodiment resides in that a part defining the aperture of the carrier contains or forms one of the two electrodes and is mounted for movement radially outwardly against a spring force.

The carrier with the electrodes can constitute a unit separate from the voltage source and the pulse generator but it is expedient to locate the battery serving as the voltage source and also the pulse generator within the carrier so that the carrier forms one self-contained unit.

Setting knobs are preferably provided on the carrier for switching the pulse generator on and off, for adjusting the amplitude and for adjusting the frequency of the pulses so that in this way individual adaptation to the user's requirements is possible.

Expediently there are diametrically opposed on the carrier two straps, one of which extends forward to the stomach while the other extends rearwardly through the crotch to the back to a belt which has to be fitted around the stomach.

This provides a simple way of separably supporting the device.

In a further development of the invention, the rearwardly extending strap has further raised electrodes in the region between scrotum and anus.

Furthermore, the rearwardly extending strap is constructed to be annular in the region of the anus and likewise contains raised electrodes in the annular part.

Also in this area there are in fact nerves responsible for functioning of the bladder closing muscle system so that in this way the action of the device according to the invention can be further enhanced.

In this respect, it is expedient to provide the strap with a kink in the region of the crotch in order to provide adaptation to the anatomy. The aperture in the region of the exit from the intestine is expedient in order not to prevent the escape of intestinal gases.

The invention will be explained in greater detail hereinafter with reference to a embodiment shown in the accompanying drawings, in which.

Figure 1:
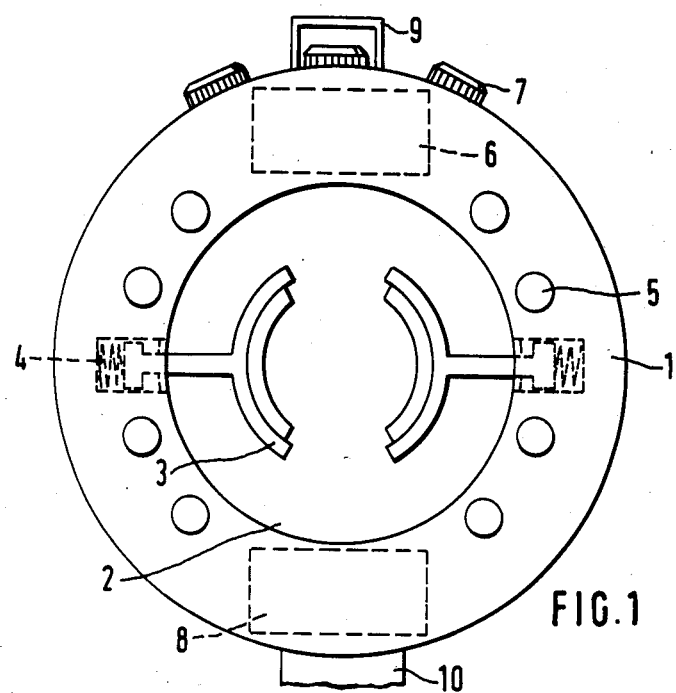
FIG. 1 is a plan view of the carrier.
Figure 2:
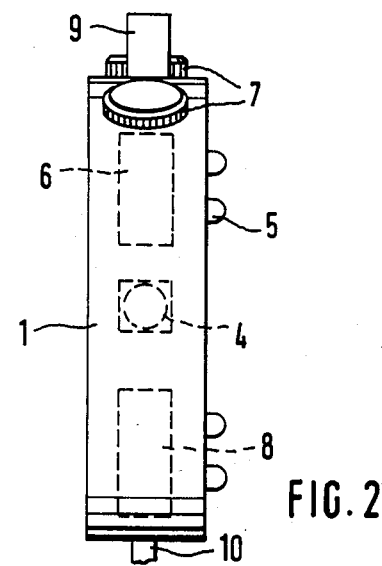
FIG. 2 is a side view of the carrier shown in FIG. 1.

FIG. 1 shows in plan view the carrier 1 which preferably consists of a skin-compatible rubber material and which is of circular construction, having an aperture 2 into which project two diametrically oppositely disposed electrodes 3. In the case of the illustrated embodiment the oppositely disposed surfaces are concave in shape. Both electrodes 3 are braced on thrust springs 4 which seek to move the electrodes 3 towards each other. In this way, the device can be pushed onto the penis, and the radial resilience permits for adaptation to the particular anatomical conditions that may be involved. Naturally, it would also be sufficient for only one of the two electrodes to be spring mounted and for the other electrode to be rigid. It may be expedient to provide in the carrier 1 an externally operable mechanism by which the two electrodes can be held in their spread-apart position in order to facilitate application of the device.

It would however also be possible to make the aperture 2 smaller and to construct a part of the carrier defining the aperture to be movable radially outwardly against a spring force. In this case, the carrier need not annularly surround the aperture; instead, the aperture can then be disposed for instance at the bottom end of a closed carrier.

The two electrodes 3 are connected to one pole of a pulse generator 6 which is supplied with current by a battery 8. Pulse generator 6 and battery 8 are thereby built into the annular carrier 1.

On that surface of the carrier 1 which faces towards the body of the person, there are a plurality of raised electrodes 5 which are connected to the other pole of the pulse generator 6 and which, when the carrier 1 is fitted, come in contact with the body of the male person so that there is a flow of current between the electrodes 3 and 5 to stimulate the bladder closure muscle tissue.

Also provided on the carrier 1 are three control knobs 7 which are connected to adjusting devices by which the pulse generator can be switched on and off and with which it is possible to adjust the amplitude and frequency of the pulses.

Preferably at the top end of the carrier 1 a lug 9 is provided and receives a strap which extends forwardly as far as the stomach. A strap 10 is attached to the bottom end of the carrier 1 and passes through the crotch to the back so that the device can be fitted to the body by means of a belt.

Figure 3:
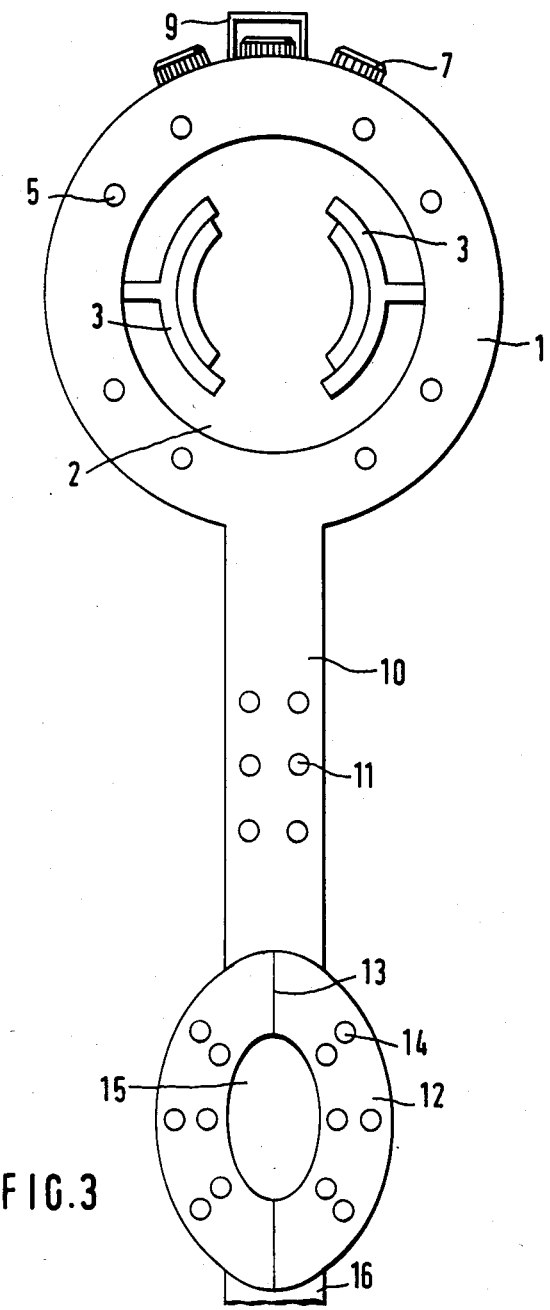
FIG. 3 is a plan view of a carrier with the strap extending to the back.
Figure 4:
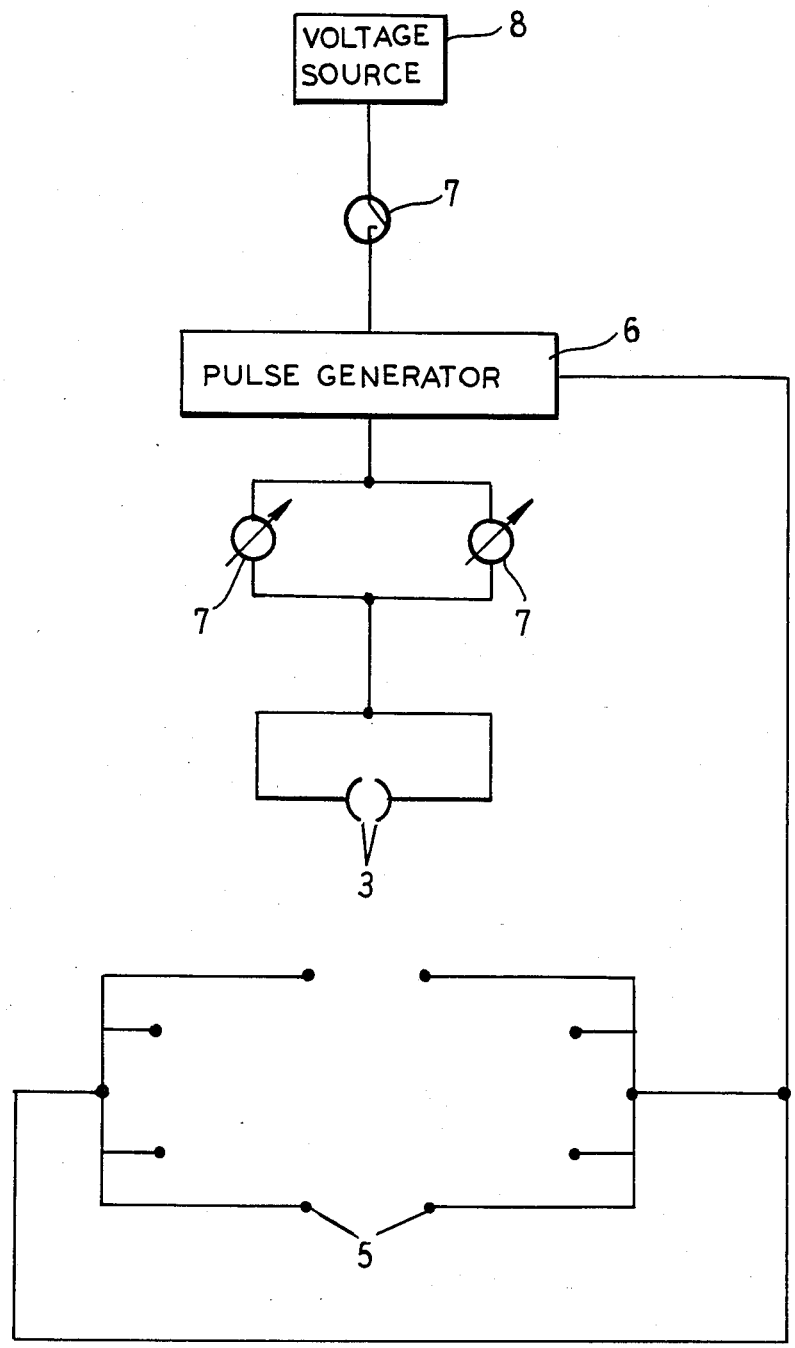
FIG. 4 is a circuit diagram of the present invention.

In FIG. 3, in which identical parts are identified by the same reference numerals as in FIG. 1, the belt 10 which extends rearwardly to the back is provided in the region extending between the scrotum and the anus with further electrodes 11 which are arranged in rows connected to separate poles of the pulse generator so that the electrodes are subject to a positive force on one side and to a negative force on the other. Thus in addition nerves which are located in this area are stimulated and influence the bladder closure muscle.

In the region of the anus, the strap 10 is widened out into a ring 12 so that it forms an opening 15 around the exit from the intestine. Electrodes 14 are also provided in this annular zone 12 and are connected to the generator 6 to stimulate the nerves located in the region of the anus and which likewise influence the closure muscle of the bladder.

It is preferable that here, too, the electrodes 14 on one side be subjected to a positive force while those on the other side are subject to a negative force.

By way of adaptation to anatomical conditions, it is expedient for the strap 10 and the annular zone 12 to be provided with a crease 13 so that they fit the shape of the crotch. Adjacent to the annular zone 12, then, is an extension 16 to the belt 10 which is connected to the supporting belt.

I claim:

1. A device for the treatment of male persons suffering from urine incontinence by an electrostimulation, said device comprising a plurality of contacts, at least two electrodes, a carrier, a voltage source, and a pulse generator forming a current source, said pulse generator being operated by said voltage source and having two poles, said carrier having a surface with the contacts being positioned thereon, said contacts being connected to one pole of said two poles, said carrier having an aperture, said aperture having means mounting each of the electrodes in said aperture, said electrodes being connected to the other pole of said two poles so that when a person wears the device with his penis inserted through the aperture and engaged by the electrodes and the contacts of the surface of the carrier engaging the body adjacent the penis, the device will stimulate the bladder closure muscle tissue.

2. A device according to claim 1, wherein the means for mounting the electrodes in the aperture mounts two electrodes and includes means to bias at least one of the electrodes towards the other electrode.

3. A device according to claim 2, wherein each of the two electrodes has a concavely curved surface facing the other electrode and are arranged symmetrically with respect to the aperture.

4. A device according to claim 3, wherein the bias means urges the two electrodes towards the center of the aperture.

5. A device according to claim 1, which includes adjustment device and control knobs disposed on the carrier, said control knobs being connected to the adjustment devices for switching on and off the pulse generator, for setting the amplitude and for setting the frequency of the pulses.

6. A device according to claim 1, wherein the carrier has an annular construction.

7. A device according to claim 6, wherein the carrier has a first strap extending from one side and diametrically opposite has a means for connection to a second strap so that the carrier can be mounted by said straps to a belt attached to the body of the patient.

8. A device according to claim 7, wherein the first strap has additional electrodes connected to the pulse generator for applying electrical stimulation in the region between the scrotum and the anus.

9. A device according to claim 8, wherein the first strap in the region of the anus has an annular portion having raised electrodes connected to the pulse generator for applying additional stimulation to the patient.

* * * * *